United States Patent [19]

Bloom et al.

[11] Patent Number: 5,614,178

[45] Date of Patent: Mar. 25, 1997

[54] COMPOSITIONS FOR TOPICAL DELIVERY OF DRUGS COMPRISING A MIXTURE OF HIGH AND LOW HLB SURFACTANTS AND ALKOXYLATED ETHER

[75] Inventors: Roberta C. Bloom, Huntington, Conn.; George E. Deckner, Cincinnati, Ohio

[73] Assignee: The Procter & Gamble Company, Cincinnati, Ohio

[21] Appl. No.: 265,975

[22] Filed: Jun. 27, 1994

Related U.S. Application Data

[63] Continuation of Ser. No. 79,977, Jun. 25, 1993, abandoned, which is a continuation-in-part of Ser. No. 33,211, Mar. 18, 1993, abandoned, which is a continuation of Ser. No. 950,527, Sep. 25, 1992, abandoned, which is a continuation-in-part of Ser. No. 920,937, Jul. 28, 1992, abandoned.

[51] Int. Cl.$^6$ .......................... A61K 7/42; A61K 31/785; A61K 7/06
[52] U.S. Cl. .......................... 424/60; 424/59; 424/70.16; 424/78.35; 424/78.02
[58] Field of Search .......................... 424/70.15, 70.16, 424/78.35, 60, 70.12

[56] References Cited

U.S. PATENT DOCUMENTS

| | | | |
|---|---|---|---|
| 3,920,810 | 11/1975 | Rankin | 424/80 |
| 4,001,392 | 1/1977 | Curry et al. | 424/70.12 |
| 4,009,256 | 2/1977 | Nowak, Jr. et al. | 424/70 |
| 4,039,501 | 8/1977 | Babcock et al. | 260/30.4 R |
| 4,318,907 | 3/1982 | Kligman et al. | 424/230 |
| 4,355,028 | 10/1982 | Kligman et al. | 424/230 |
| 4,540,568 | 9/1985 | Trager et al. | 424/81 |
| 4,599,379 | 7/1986 | Flesher et al. | 524/801 |
| 4,608,370 | 8/1986 | Aronsohn | 514/159 |
| 4,628,078 | 12/1986 | Glover et al. | 526/303.1 |
| 4,673,704 | 6/1987 | Flesher et al. | 524/519 |
| 4,704,436 | 11/1987 | Barabas | 525/326.9 |
| 4,795,643 | 1/1989 | Seth | 424/456 |
| 4,806,345 | 2/1989 | Bhattacharyya | 424/70 |
| 4,835,206 | 5/1989 | Farrar et al. | 524/457 |
| 4,837,019 | 6/1989 | Georgalas et al. | 424/101 |
| 4,849,484 | 7/1989 | Heard | 525/221 |
| 4,885,161 | 12/1989 | Cornell | 424/78 |
| 4,915,940 | 4/1990 | Saitoh et al. | 424/81 |
| 4,929,577 | 5/1990 | Cornell | 514/58 |
| 5,009,969 | 4/1991 | Miller | 424/59 |
| 5,017,367 | 5/1991 | Stojkoski | 424/63 |
| 5,051,251 | 9/1991 | Morita et al. | 424/70 |
| 5,100,660 | 3/1992 | Hawe et al. | 424/78.35 |
| 5,182,105 | 1/1993 | Takata et al. | 424/78.02 |
| 5,221,530 | 6/1993 | Janchitraponveg et al. | 424/70 |
| 5,232,688 | 8/1993 | Ziegler et al. | 424/59 |

FOREIGN PATENT DOCUMENTS

| | | |
|---|---|---|
| 067658 | 6/1982 | European Pat. Off. . |
| 228868 | 12/1986 | European Pat. Off. . |
| 312208 | 9/1988 | European Pat. Off. . |
| 2071745 | 6/1982 | Japan . |
| 57-091913 | 3/1990 | Japan . |
| 2236760 | 10/1990 | United Kingdom . |
| 93/07856 | 4/1993 | WIPO . |
| 93/07903 | 4/1993 | WIPO . |
| 93/07902 | 4/1993 | WIPO . |

OTHER PUBLICATIONS

Technical Bulletin—Salcare SC 92 for Cosmetic/Personal Care Applications, Allied Colloids, Suffolk, VA—undated.
Technical Bulletin—Salcare SC91: The Cosmetic Formulators's Choice For Anionic Skin Care Products Allied Colloids, Suffolk, VA—undated.
08/059,001 Deckner et al. May 6, 1993.
07/948,391 Deckner et al. Sep. 25, 1992.
07/778,422 Deckner et al. Oct. 16, 1991.
07/931,553 Deckner et al. Aug. 18, 1992.
07/778,423 Deckner et al. Oct. 16, 1991.
08/111,032 Deckner et al. Aug. 24, 1993.
07/957,752 Deckner et al. Oct. 02, 1992.
07778424 Deckner et al. Oct. 16, 1992.

*Primary Examiner*—Peter F. Kulkosky
*Attorney, Agent, or Firm*—Anthony D. Sabatelli; David K. Dabbiere

[57] ABSTRACT

The present invention relates to pharmaceutical compositions for topical application comprising a safe and effective amount of a pharmaceutical active, from about 0.1% to about 10.0% of a high molecular weight cationic polymer, from about 0.05% to about 5% of a high HLB non-ionic surfactant, and from about 0.1% to about 25% of an alkoxylated ether. In further embodiments, these compositions also comprise from about 0.01% to about 5% of a low HLB non-ionic surfactant.

45 Claims, No Drawings

COMPOSITIONS FOR TOPICAL DELIVERY OF DRUGS COMPRISING A MIXTURE OF HIGH AND LOW HLB SURFACTANTS AND ALKOXYLATED ETHER

This is a continuation of application Ser. No. 08/079,977, filed on Jun. 25, 1993, now abandoned, which is a continuation-in-part of application Ser. No. 08/033 211, filed on Mar. 18, 1993 now abandoned, which is a continuation of Ser. No. 07/950,527 filed on Sep. 25, 1992, now abandoned which is a continuation-in-part of Ser. No. 07/920,937 filed on Jul. 28, 1992, now abandoned.

TECHNICAL FIELD

The present invention relates to compositions for the topical administration of drugs, especially such compositions having enhanced penetration of the drug through the skin.

BACKGROUND OF THE INVENTION

Because of the accessibility and large area of the skin, it has long been considered a promising route for the administration of drugs, whether dermal, regional, or systemic effects are desired.

The advantages of the topical route of drug administration include: avoidance of the risks and inconvenience of parenteral treatment; avoidance of the variable absorption and metabolism associated with oral treatment; continuity of drug administration, permitting use of pharmacologically active agents with short biological half-lives; potential reduction of gastrointestinal irritation in systemic administration; and treatment of cutaneous manifestations of diseases usually treated systemically.

However, the impermeability of skin is well-known, serving as a barrier to ingress of pathogens and toxic chemicals, and egress of physiologic fluids. This impermeability is the result of normal physiologic changes in developing skin. A typical cell in the epidermis is formed in the basal layer. It typically takes approximately thirty days for a cell to migrate from the basal layer of the epidermis to sloughing off and discarding at the outer layers of the stratum corneum. As the cell migrates outward from the basal layer, it progressively keratinizes until it is relatively impermeable. The result is the stratum corneum, an extremely thin surface layer (10 microns) with substantial barrier properties. The cell envelopes of the cells in the stratum corneum tend to be mainly polar lipids, such as ceramides, sterols, and fatty acids while the cytoplasm of stratum corneum cells remains polar and aqueous. Despite the close packing of the cells, some 15% of the stratum corneum is intercellular and, generally, lipid based. It is generally recognized that over the very short term, penetration occurs through the hair follicles and the sebaceous apparatus; long-term penetration occurs across cells (non-polar route). Poor penetration of many drugs across the epidermal lipid barrier has, until now, frustrated attempts to deliver clinically significant doses of many drugs by the topical route.

One route of delivery of drugs is by transdermal administration. Transdermal administration of drugs can be used in many instances to achieve therapeutic levels of the drugs in the systemic circulatory system, as well as for more localized internal dosing of drugs. Where such therapeutic levels of drugs can be achieved by transdermal administration, several potential advantages exist over other routes of administration. Sustained systemic delivery of drug controlled at therapeutic but below toxic levels over long periods of time with a single continuous application is often an advantage of transdermal drug administration. Potential contamination of internal tissues with undesired foreign substances or microbes, often associated with parenteral administration of drugs, is avoided with transdermal drug administration. Oral administration of many drugs is undesirable or unfeasible because the drug decomposes in the harsh environment of the gastrointestinal tract, lacks sufficient absorption from the gastrointestinal tract, or causes gastrointestinal upset or tissue damage in the gastrointestinal tract. First-pass metabolism of orally administered drugs can increase the dosage required to achieve therapeutic levels and thereby increase undesirable side effects either from the primary drug or the metabolites. Maintenance of uniform, optimal systemic levels of drugs for long periods of time is often difficult through oral administration. Such problems can often be reduced or avoided by transdermal drug administration.

Despite the substantial potential advantages for transdermal administration of drugs, relatively few drugs are so administered. The skin is a formidable barrier to the passage of most drugs. It is often necessary to provide a composition containing a skin penetration enhancing vehicle in order to provide sufficient transdermal penetration of the drug to achieve therapeutic levels of the drug at the target internal tissue. A number of skin penetration enhancing vehicles for drugs have been disclosed, including those in the following references: U.S. Pat. No. 3,536,816 issued to Kellner on Oct. 27, 1970; U.S. Pat. No. 4,006,218 issued to Sipos on Feb. 1, 1977; U.S. Pat. No. 4,124,720 issued to Wenmaekers on Nov. 7, 1978; U.S. Pat. No. 4,126,681 issued to Reller on Nov. 21, 1978; U.S. Pat. No. 4,299,826 issued to Luedders on Nov. 10, 1981; U.S. Pat. No. 4,305,936 issued to Klein on Dec. 15, 1981; U.S. Pat. No. 4,309,414 issued to Inagi, Muramatsu & Nagai on Jan. 5, 1982; U.S. Pat. No. 4,338,306 issued to Kitao & Nishimura on Jul. 6, 1982; U.S. Pat. No. 4,442,090 issued to Kakeya, Kitao & Nishimura on Apr. 10, 1984; U.S. Pat. No. 4,485,033 issued to Kitao & Nishimura on Nov. 27, 1984; U.S. Pat. No. 4,537,776 issued to Cooper on Aug. 27, 1985; U.S. Pat. No. 4,552,872 issued to Cooper, Loomans & Fawzi on Nov. 12, 1985; U.S. Pat. No. 4,557,934 issued to Cooper on Dec. 10, 1985; U.S. Pat. No. 4,573,995 issued to Chen, Chun & Enscore on Mar. 4, 1986; U.S. Pat. No. 4,626,539 issued to Aungst & DiLuocio on Dec. 2, 1986; U.S. Pat. No. 4,637,930 issued to Konno, Kawata, Aruga, Sonobe & Mitomi issued Jan. 20, 1987; U.S. Pat. No. 4,695,465 issued to Kigasawa, Ohtani, Tanaka & Hayashida on Sep. 22, 1987; European Patent Application No. 0,043,738 of The Procter & Gamble Company in the names of Wickett, Cooper & Loomans, published on Jun. 13 1982; European Patent Application No. 0,095,813 of The Procter & Gamble Company in the name of Cooper, published Dec. 7, 1983; PCT International Patent Application No. WO 87/03490 of Key Pharmaceuticals, Inc. in the names of Bodor and Loftson, published on Jun. 18, 1987; Washitake, M., T. Anmo, I. Tanaka, T. Arita & M. Nakano, "Percutaneous Absorption of Drugs from Oily Vehicles", *Journal of Pharmaceutical Sciences*, Vol. 64, No. 3 (March, 1975), pp. 397–401; Shahi, V., & J. L. Zatz, "Effect of Formulation Factors on Penetration of Hydrocortisone through Mouse Skin", *Journal of Pharmaceutical Sciences*, Vol. 67, No. 6 (June, 1978), pp. 789–792; Cooper, E. R., "Increased Skin Permeability for Lipophilic Molecules", *Journal of Pharmaceutical Sciences*, Vol. 73, No. 8 (August, 1984), pp. 1153–1156; Aungst, B. J., N. J. Rogers & E. Shefter, "Enhancement of Naloxone Penetration through Human Skin In Vitro Using Fatty Acids, Fatty Alcohols, Surfactants, Sulfoxides and Amides", *International Journal of Pharmaceutics*, Vol. 33 (1986), pp. 225–234; Green, P. G., & J. Hadgraft, "Facilitated Transfer of Cationic Drugs Across a Lipoidal Membrane by Oleic Acid and Lauric Acid", *International Journal of Pharmaceutics*, Vol. 37 (July, 1987), pp. 251–255.

Often, though, transdermal delivery of drugs can cause skin irritation (e.g., burning and stinging), drying of skin and further can be difficult to formulate. The present invention provides stable compositions for the transdermal delivery of drugs which do not require ethanol to solubilize the active and therefore can be substantially free of ethanol, are easy to formulate and which further provide low dermal irritation. These compositions also provide improved moisturizing benefits.

It is an object of the present invention to provide novel compositions for enhancing the skin penetration of drugs with significantly reduced skin irritation.

It is a further object of the present invention to provide such compositions which provide sufficient skin penetration enhancement to achieve therapeutic levels of the drugs in target internal tissues.

It is a further object of the present invention to provide such compositions with low dermal irritation, especially in compositions requiring a low pH.

It is a further object of the present invention to provide such compositions having good stability and good cosmetics and which do not require ethanol to solubilize the drug actives.

It is a further object of the present invention to provide compositions useful for the treatment of acne.

It is a further object of the present invention to provide compositions useful for the treatment of skin wrinkles and skin atrophy and other affects of skin aging such as actinic elastosis.

SUMMARY OF THE INVENTION

The present invention relates to pharmaceutical compositions for topical application having enhanced penetration through the skin comprising:

(a) a safe and effective amount of a pharmaceutical active;

(b) from about 0.1% to about 10.0% of a high molecular weight crosslinked cationic polymer of the formula: $(A)_l(B)_m(C)_n$ wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer having one carbon-carbon double bond, l is an integer of 0 or greater, m is an integer of 1 or greater, and n is an integer of 0 or greater, wherein said polymer contains a crosslinking agent;

(c) from about 0.05% to about 5% of a high HLB non-ionic surfactant; and (d) from about 0.1% to about 25% of an alkoxylated ether of the formula:

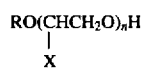

wherein R is straight or branched chain $C_1$ to $C_{18}$, preferably $C_1$ to $C_{10}$ and most preferably $C_1$ to $C_5$, and X is methyl or ethyl, and wherein n is an average of from about 5 to about 20.

In further embodiments the compositions comprise from about 0.01% to about 5% of a low HLB non-ionic surfactant.

In even further embodiments the crosslinked cationic polymer is of the formula wherein (C) is acrylamide.

In even further embodiments the crosslinked cationic polymer is of the formula wherein (C) is acrylamide and l is zero.

In even further embodiments the crosslinked cationic polymer is a homopolymer wherein both l and n are zero.

All concentrations and ratios herein are by weight of total composition and all measurements are at 25° C. unless otherwise specified.

These compositions are preferably substantially free of ethanol. By substantially free of ethanol is meant the compositions comprise less than about 5%, preferably less than about 1% and most preferably less than about 0.5% ethanol.

The invention hereof can comprise, consist of, or consist essentially of, the essential as well as optional ingredients and components described herein.

DETAILED DESCRIPTION OF THE INVENTION

The present invention involves compositions comprising certain specific cationic polymers, nonionic surfactant and water-immiscible solubilizing aids which may be applied topically to the skin and which result in improved transdermal delivery (i.e. optimized penetration) of the drugs through the skin. These compositions do not need additional solvents such as ethanol to solubilize the active in the compositions.

Drug Active

The compositions of the present invention comprise a safe and effective amount of a drug active. The phrase "safe and effective amount", as used herein, means an amount of a drug high enough to significantly positively modify the condition to be treated, but low enough to avoid serious side effects (at a reasonable benefit/risk ratio), within the scope of sound medical judgement. A safe and effective amount of the drug will vary with the specific drug, the ability of the composition to penetrate the drug through the skin, the amount of composition to be applied, the particular condition being treated, the age and physical condition of the patient being treated, the severity of the condition, the duration of the treatment, the nature of concurrent therapy, and like factors.

The drug compounds present in the compositions of the present invention preferably comprise from about 0.1% to about 20% by weight of the compositions, more preferably from about 0.1% to about 10%, and most preferably from about 0.1% to about 5%. Mixtures of drug actives may also be used. It is contemplated herein that the various actives described below can provide more than one benefit and can alternatively be classified under more than one category, below.

Useful drug actives in the compositions of the present invention include anti-acne drugs. Anti-acne drugs preferred for use in the present invention include the keratolytics such as salicylic acid, sulfur, lactic acid, glycolic, pyruvic acid, urea, resorcinol, and N-acetylcysteine; retinoids such as retinoic acid and its derivatives (e.g., cis and trans); antibiotics and antimicrobials such as benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate, and cholate. Preferred for use herein is salicylic acid. Without being limited by theory, even though salicylic acid is classified herein as a an anti-acne agent, it is also useful for other skin benefits such as anti-wrinkling and anti-skin atrophy benefits which are described in the following paragraph.

Useful drug actives in the compositions of the present invention include anti-wrinkle and anti-skin atrophy actives which include the C2–C30 alpha-hydroxy acids (e.g., glycolic acid, lactic acid, 2-hydroxybutanoic acid, and the like), retinoic acid, salicylic acid, and skin peel agents (e.g., phenol, acetic acid, and the like). Preferred for use herein are glycolic acid, lactic acid, salicylic acid, and mixtures thereof.

Useful drug actives in the compositions of the present invention include non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Useful drug actives in the compositions of the present invention include antihistaminic drugs. Antihistaminic drugs preferred for inclusion in compositions of the present invention include pharmaceutically-acceptable salts of chlorpheniramine, triprolidine, diphenhydramine, doxylamine, pyrilamine, phenindamine, promethazine, cyproheptadine, azatadine, clemastine, carbinoxamine, tripelennamine, terfenadine, dexchlorpheniramine, brompheniramine, chlorcyclizine, diphenylpyraline, pheniramine and phenyltoloxamine, and mixtures thereof.

Useful drug actives in the compositions of the present invention include antitussive drugs. Antitussive drugs preferred for inclusion in compositions of the present invention include pharmaceutically-acceptable salts of dextromethorphan, codeine, caramiphen and carbetapentane.

Useful drug actives in the compositions of the present invention include antipruritic drugs. Antipruritic drugs preferred for inclusion in compositions of the present invention include pharmaceutically-acceptable salts of methdilizine and trimeprazine.

Useful drug actives in the compositions of the present invention include anticholinergic drugs. Anticholinergic drugs preferred for inclusion in compositions of the present invention include pharmaceutically-acceptable salts of scopolamine, atropine, homatropine, levodopa, dicyclomine, hyoscyamine, procyclidine, trihexyphenidyl and ethopropazine.

Useful drug actives in the compositions of the present invention include anti-emetic and antinauseant drugs. Anti-emetic and antinauseant drugs preferred for inclusion in compositions of the present invention include pharmaceutically-acceptable salts of cyclizine, meclizine, chlorpromazine, buclizine, metoclopramide, prochlorperazine and trimethobenzamide.

Useful drug actives in the compositions of the present invention include anorexic drugs. Anorexic drugs preferred for inclusion in compositions of the present invention include pharmaceutically-acceptable salts of benzphetamine, phentermine, chlorphentermine, fenfluramine, diethylpropion and phendimetrazine.

Useful drug actives in the compositions of the present invention include central stimulant drugs. Central stimulant drugs preferred for inclusion in compositions of the present invention include pharmaceutically-acceptable salts of amphetamine, methamphetamine, dextroamphetamine and methylphenidate.

Useful drug actives in the compositions of the present invention include antiarrhythmic drugs. Antiarrhythmic drugs preferred for inclusion in compositions of the present invention include pharmaceutically-acceptable salts of propranolol, procainamide, disopyramide, quinidine, encainide, flecanaide, mexiletine and tocainide. Other antiarrhythmic drugs preferred for inclusion in compositions of the present invention include pharmaceutically-acceptable salts of the quinidine derivatives disclosed in U.S. Pat. No. 4,716,171 issued to Jarreau and Koenig on Dec. 29, 1987, which is hereby incorporated herein in its entirety by reference. Highly preferred compounds included in this class include pharmaceutically-acceptable salts of 3S-hydroxy-10,11-dihydroquinidine, 3R-hydroxy-10,11-dihydroquinidine, 3R-hydroxy-0-acetyl-10,11-dihydroquinidine, and 3S-hydroxy-0-acetyl-10,11-dihydroquinidine, especially 3S-hydroxy-10,11-dihydroquinidine.

Useful drug actives in the compositions of the present invention include β-adrenergic blocker drugs. β-Adrenergic blocker drugs preferred for inclusion in compositions of the present invention include pharmaceutically-acceptable salts of metoprolol, acebutolol, betaxolol, labetalol and timolol. β-Adrenergic blocker drugs more preferred for inclusion in compositions of the present invention include metoprolol tartrate, acebutolol hydrochloride, betaxolol hydrochloride, labetalol hydrochloride and timolol maleate.

Useful drug actives in the compositions of the present invention include cardiotonic drugs. Cardiotonic drugs preferred for inclusion in compositions of the present invention include pharmaceutically-acceptable salts of milrinone, amrinone and dobutamine. Other cardiotonic drugs preferred for inclusion in compositions of the present invention include pharmaceutically-acceptable salts of 14-amino steroid derivatives, some of which are disclosed in U.S. Pat. Nos. 4,325,879, 4,552,868 and 4,584,289, issued to Jarreau and Koenig on Apr. 20, 1982, Nov. 12, 1985 and Apr. 22, 1986, respectively, each of which are hereby incorporated herein in their entirety by reference.

Useful drug actives in the compositions of the present invention include antihypertensive drugs. Antihypertensive drugs preferred for inclusion in compositions of the present invention include pharmaceutically-acceptable salts of enalapril, clonidine, hydralazine, minoxidil (which is also a hair growth stimulator drug), guanadrel, guanethidine, guanfacine, mecamylamine, methyldopate, pargyline, phenoxybenzamine and prazosin.

Useful drug actives in the compositions of the present invention include diuretic drugs. Diuretic drugs preferred for inclusion in compositions of the present invention include pharmaceutically-acceptable salts of amiloride and hydrochlorothiazide. Diuretic drugs more preferred for inclusion in compositions of the present invention include amiloride hydrochloride.

Useful drug actives in the compositions of the present invention include vasodilator drugs. Vasodilator drugs preferred for inclusion in compositions of the present invention include pharmaceutically-acceptable salts of diltazem, amiodarone, isoxsuprine, nylidrin, tolazoline and verapamil.

Useful drug actives in the compositions of the present invention include vasoconstrictor drugs. Vasoconstrictor drugs preferred for inclusion in compositions of the present invention include pharmaceutically-acceptable salts of dihydroergotamine, ergotamine and methysergide.

Useful drug actives in the compositions of the present invention includes anti-ulcer drugs. Anti-ulcer drugs preferred for inclusion in compositions of the present invention include pharmaceutically-acceptable salts of ranitidine and cimetidine.

Useful drug actives in the compositions of the present invention include include anesthetic drugs. Anesthetic drugs preferred for inclusion in compositions of the present invention include pharmaceutically-acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Useful drug actives in the compositions of the present invention include antidepressant drugs. Antidepressant drugs preferred for inclusion in compositions of the present invention include pharmaceutically-acceptable salts of imipramine, desipramine, amitriptyline, nortriptyline, protriptyline, doxepin, maprotiline, phenelzine, tranylcypromine, trazodone and trimipramine.

Useful drug actives in the compositions of the present invention include tranquilizer and sedative drugs. Tranquilizer and sedative drugs preferred for inclusion in compositions of the present invention include pharmaceutically-acceptable salts of chlordiazepoxide, benactyzine, benzquinamide, flurazepam, hydroxyzine, loxapine and promazine.

Useful drug actives in the compositions of the present invention include antipsychotic drugs. Antipsychotic drugs preferred for inclusion in compositions of the present invention include pharmaceutically-acceptable salts of chlorprothixene, fluphenazine, haloperidol, molindone, thioridazine and trifluoperazine.

Useful drug actives in the compositions of the present invention include antimicrobial drugs (antibacterial, antifungal, antiprotozoal and antiviral drugs). Antimicrobial drugs preferred for inclusion in compositions of the present invention include pharmaceutically-acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole and amanfadine. Antimicrobial drugs preferred for inclusion in compositions of the present invention include tetracycline hydrochloride, erythromycin estolate, erythromycin stearate (salt), amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole.

Useful drug actives in the compositions of the present invention include antineoplastic drugs. Antineoplastic drugs preferred for inclusion in compositions of the present invention include pharmaceutically-acceptable salts of bleomycin, daunorubicin, doxorubicin, mechlorethamine, procarbazine, quinacrine, tamoxifen, vinblastine and vincristine.

Useful drug actives in the compositions of the present invention include antimalarial drugs. Antimalarial drugs preferred for inclusion in compositions of the present invention include pharmaceutically-acceptable salts of chloroquine, hydroxychloroquine primaquine and quinine.

Useful drug actives in the compositions of the present invention include muscle relaxant drugs. Muscle relaxant drugs preferred for inclusion in compositions of the present invention include pharmaceutically-acceptable salts of cinnamedrine, cyclobenzaprine, flavoxate, orphenadrine, papaverine, mebeverine, idaverine, ritodrine, dephenoxylate, dantrolene and azumolene.

Useful drug actives in the compositions of the present invention include antispasmodic drugs. Antispasmodic drugs preferred for inclusion in compositions of the present invention include pharmaceutically-acceptable salts of the compounds disclosed in U.S. Pat. No. 3,856,825 issued to Wright, Burch and Goldenburg on Dec. 24, 1974, which is hereby incorporated herein in its entirety by reference.

Useful drug actives in the compositions of the present invention include antidiarrheal drugs. Antidiarrheal drugs preferred for inclusion in compositions of the present invention include pharmaceutically-acceptable salts of loperamide.

Useful drug actives in the compositions of the present invention include bone-active drugs. Bone-active drugs preferred for inclusion in compositions of the present invention include pharmaceutically-acceptable salts of diphosphonate drug compounds and phosphonoalkylphosphinate drug compounds, including the prodrug esters thereof. Such compounds are disclosed, for example, in U.S. Pat. Nos. 3,683,080 issued to Francis on Aug. 8, 1972; U.S. Pat. No. 4,304,734 issued to Jary, Rihakova & Zobacova on Dec. 8, 1981; U.S. Pat. No. 4,687,768 issued to Benedict & Johnson on Aug. 18, 1987; U.S. Pat. No. 4,711,880 issued to Stahl & Schmitz on Dec. 8, 1987; and U.S. Pat. No. 4,719,203 issued to Bosies & Gall on Jan. 12, 1988; copending U.S. patent application Ser. Nos. 808,584, of Benedict & Perkins filed Dec. 13, 1985 now U.S. Pat. No 4,902,679; Ser. No. 945,069 of Ebetino, Buckingham & McOsker filed Dec. 19, 1986 now U.S. Pat No. 4,868,164; Ser. No. 945,068 of Ebetino & Benedict filed Dec. 19, 1986 now abandoned; and Ser. No. 069,666 of Ebetino filed Jul. 6, 1987 now abandoned; and European Patent Application Nos. 0,001,584 of Blum, Hempel & Worms, published May 2, 1979; 0,039,033 published Apr. 11, 1981; 0,186,405 of Benedict & Perkins, published Jul. 2, 1986; and 0,243,173 of Oku, Todo, Kasahara, Nakamura, Kayakiri & Hashimoto, published Oct. 28, 1987; all of which are hereby incorporated herein in their entirety by reference.

Also useful in the present invention sunscreening agents. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety.

Preferred among those sunscreens which are useful in the compositions of the instant invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl)methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy)dibenzoylmethane, and mixtures thereof.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Registor*, Vol. 43, No. 166, pp. 38206–38269, Aug. 25, 1978, which is incorporated herein by reference in its entirety.

Also useful in the present invention are sunless tanning agents including dihydroxyacetone, glyceraldehyde, indoles and their derivatives, and the like. These sunless tanning agents can also be used in combination with the sunscreen agents.

Other useful actives include skin bleaching (or lightening) agents including but not limited to hydroquinone, ascorbic acid, kojic acid and sodium metabisulfite and wound healing agents such as peptide derivatives, yeast, panthenol, Iamin and kinetin.

Water-Soluble Polymer

The polymers useful in the present invention are certain cationic polymers. These polymers are generally described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein.

The compositions of the instant invention comprise from about 0.1% to about 10%, preferably from about 0.1% to about 7.5%, and most preferably from about 0.1% to about 5% of the polymer.

In general these polymers are high molecular weight materials containing cationic, usually quaternized, nitrogen moieties. These polymers can be characterized by the general formula: $(A)_l(B)_m(C)_n$ wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer having one carbon—carbon double bond, l is an integer of 0 or greater, m is an integer of 1 or greater, and n is an integer of 0 or greater. The (C) monomer can be selected from any of the commonly used monomers. Nonlimiting examples of these monomers include ethylene, propylene, butylene, isobutylene, eicosene, maelic anhydride, acrylamide, methacrylamide, maleic acid, acrolein, cycohexene, ethyl vinyl ether, and methyl vinyl ether. In the cationic polymers of the present invention, (C) is preferably acrylamide.

In highly preferred embodiments, these polymers also contain a crosslinking agent, which is most typically a material containing one or more unsaturated functional groups. In other words, these crosslinked polymers are expressly intended to also include the corsslinking agent in addition to the (A), (B), and (C) monomer units. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a cosslinking agent is methylenebisacrylamide.

When the croslinking agent is present, widely varying amounts can be employed depending upon the properties desired in the final polymer, e.g. viscosifying effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about about 500 ppm of the total weight of the polymer on a weight/weight basis.

In one group of embodiments, these cationic polymers are made from processes which generally require polymerisation of a solution containing from about 20% to about 60%, generally from about 25% to about 40%, by weight monomer, in the presence of an initiator (usually redox or thermal) until the polymerization terminates. The temperature generally starts low, e.g. 0° to 95° C. The polymerization can be conducted by forming a reverse phase dispersion of an aqueous phase of the monomers into a nonaqueous liquid, e.g. mineral oil and the like.

When the polymer contains acrylamide, the molar proportion of acrylamide, based on the total molar amount of acrylamide, dialkylaminoalkyl acrylate and dialkylaminoalkyl methacrylate, is generally from about 20% to about 99%. Preferably, the amount of acrylamide is at least 50%, often at least 60% to below about 95%.

All percentages describing the polymer herein are molar, unless otherwise specified.

Where monomer A is present, the ratio of monomer A:monomer B used in this process, and thus the ratio of groups A and B in the final polymer, on a molar basis is preferably about 80:20 to about 20:80. In one class of processes, the ratio is about 5:95 to 50:50, i.e., the cationic monomer is mainly methacrylate. In these processes, the ratio is generally being achieved in the range of from about 25:75 to about 5:95.

In another class of processes, the ratio A:B is from about 50:50 to about 85:15, the cationic monomers being mainly acrylate. Preferably the ratio A:B is about 60:40 to 85:15, most preferably about 75:25 to 85:15.

Preferred is where monomer A is not present and the ratio of monomer B:monomer C is from about 30:70 to about 70:30, preferably from about 40:60 to about 60:40 and most preferably from about 45:55 to about 55:45.

The polymerisation is preferably conducted under known conditions such that the polymers are water soluble and have a high molecular weight, generally about 1 million, for instance up to 30 million. The intrinsic viscosity, measured in molar sodium chloride solution at 25° C., is generally above 6, for instance from 8 to 14.

A cationic polymer useful herein is one conforming to the general structure $(A)_l(B)_m(C)_n$ wherein l is zero, (B) is methyl quaternized dimethylaminoethyl methacrylate, the ratio of (B):(C) is about 45:55 to about 55:45, and the optional crosslinking agent is methylenebisacrylamide. This polymer which has the proposed CTFA designation, "Polyquaternium 32 (and) Mineral Oil", is commercially available as Salcare SC92 from Allied Colloids Ltd. (Norfolk, Va.).

Alternatively in another group of preferred embodiments, these cationic polymers do not contain the acrylamide monomer, that is, n is zero. In these polymers the (A) and (B) monomer components are as described above. An especially preferred group Of these non-acrylamide containing polymers is one in which l is also zero. In this instance the polymer is essentially a homopolymer of a dialkylaminoalkyl methacrlyate monomer or its quaternary ammonium or acid addition salt. These diaklylaminoalkyl methacrylate copolymers and homopolymers preferably contain a crosslinking agent as described above.

A cationic homopolymer useful herein is one conforming to the general structure $(A)_l(B)_m(C)_n$ wherein l is zero, (B) is methyl quaternized dimethylaminoethyl methacrylate, n is zero, and the crosslinking agent is methylenebisacrylamide. This polymer, which has recently been given CTFA designation "Polyquaternium 37 (and) Mineral Oil (and) PPG-1 Trideceth-6", will be referred to herein as crosslinked methyl quaternized dimethylaminoethyl methacrylate and mineral oil. This polymer is commercially available as Salcare SC95 from Allied Colloids Ltd. (Norfolk, Va.).

Nonionic Surfactant

Compositions of this invention also contain from about 0.05% to about 10%, preferably from about 0.05% to about 5%, more preferably from about 0.05% to about 2%, and most preferably from about 0.25% to about 1% of certain nonionic surfactants. Nonionic surfactants useful herein include any of the well-known nonionic surfactants that have an HLB of from about 6 to about 18, preferably from about 8 to about 18, and more preferably from about 10 to about 18. These nonionic surfactants are herein designated as "high HLB nonionic surfactants" and do not include the surfactants with HLB values less than 6, as described below.

The abbreviation "HLB" stands for hydrophilic lipophilic balance. The HLB system is well known in the art and is described in detail in "The HLB System, A Time-Saving Guide to Emulsifier Selection", ICI Americas Inc., August 1984, which is incorporated herein by reference.

Typical of these high HLB nonionic surfactants are ethoxylated or propoxylated, preferably ethoxylated, alcohols and alkyl phenols, with the alcohol derivatives being preferred. In general, these alcohol derivatives contain a straight or branched chain alkyl group in the $C_{8-22}$, preferably $C_{10-20}$, more preferably $C_{12-20}$, range and generally contain from about 6 to about 30, preferably from about 6 to about 25, ethylene oxide or propylene oxide groups. Among these ethoxylated and propoxylated alcohols, the ethoxylated derivatives are most preferred.

Preferred for use herein are polyethylene oxide ethers derived from lauryl alcohol, cetyl alcohol, oleyl alcohol, stearyl alcohol, isostearyl alcohol, myristyl alcohol, behenyl alcohol, and mixtures thereof. More preferred for use herein are: polyoxyethylene 10 cetyl ether, known by the CTFA designation as ceteth-10; polyoxyethylene (21) stearyl ether, known by the CTFA designation steareth-21; coconut alkyl polyethoxylate (6.5); decyl polyethoxylate (6); and mixtures thereof. Most preferred for use herein are ceteth-10, steareth-21, and mixtures thereof.

A detailed listing of suitable nonionic surfactants, of the above types, for the compositions herein can be found in U.S. Pat. No. 4,557,853, to Collins, issued Dec. 10, 1985, which is incorporated by reference herein. Commercial sources of such surfactants can be found in McCutcheon's EMULSIFIERS AND DETERGENTS, North American Edition, 1984, McCutcheon Division, MC Publishing Company, also incorporated herein by reference.

Especially preferred for use herein are compositions which contain at least one of the above described high HLB nonionic surfactants, in combination with at least one other nonionic surfactant having an HLB from about 1 to about, but not greater than or equal to 6, hereinafter designated as a "low HLB nonionic surfactant". These low HLB nonionic surfactants do not include the high HLB nonionic surfactants described above. Without being limited by theory, it is believed that this combination of both high and low HLB nonionic surfactants provides compositions demonstrating enhnaced emulsion stability.

In these compositions utilizing both the low HLB nonionic surfactant in combination with the high HLB nonionic surfactant, the low HLB nonionic surfactant comprises from about 0.01% to about 5%, preferably from about 0.01% to about 1%, and more preferably from about 0.025% to about 0.5% of the composition.

Typical of these low HLB nonionic surfactants are ethoxylated alcohols with the alcohol derivatives being preferred. In general, these alcohol derivatives contain a straight or branched chain alkyl group in the $C_{8-22}$, preferably $C_{10-20}$, more preferably $C_{12-20}$, range, and generally contain from about 1 to about 5 ethylene oxide groups per molecule.

Some nonlimiting examples of these low HLB nonionic surfactants useful herein include stearic acid ethoxylated with 1 mole of ethylene oxide (i.e. steareth-1), steareth-2, steareth-3, steareth-4, steareth-5, ceteth-1, cetheth-2, ceteth-3, ceteth-4, ceteth-5, laureth-1, laureth-2, laureth-3, laureth-4, laureth-5, oleic acid ethoxylated with 1 mole or ethylene oxide (i.e. oleth-1), oleth-2, oleth-3, oleth-4, oleth-5, and mixtures thereof. Preferred low HLB nonionic surfactants are steareth-1, steareth-2, steareth-3, ceteth-1, ceteth-2, cetheth-3, laureth-1, laureth-2, laureth-3, oleth-1, oleth-2, oleth-3, and mixtures thereof. More preferred are steareth-2, ceteth-2, laureth-2, oleth-2, and mixtures thereof. Most preferred is steareth-2, which is available commercially as Brij 72 from ICI Americas.

Detailed listings of low HLB surfactants can be found in McCutcheon's EMULSIFIERS AND DETERGENTS, North American Edition, 1984, McCutcheon Division, MC Publishing Company, which has already been incorporated herein by reference.

When a low HLB nonionic surfactant in used herein in combination with a high HLB surfactant, it has been found that the combination of steareth-2 with ceteth-10 and/or steareth-21 is especially preferred.

Water-Immiscible Solubilizing Aid

The compositions of the present invention comprise preferably from about 0.1% to about 25%, more preferably from about 0.1% to about 15%, and most preferably from about 6% to about 10% of a water-immiscible solubilizing aid for the active ingredients useful herein. By water-immiscible is meant that the material has a solubility in water of less than 1 gram per 100 grams of water at 25° C. Without being limited by theory, these materials improve the stability of the composition as well as provide moisturization benefits. In particular, two classes of these water-immiscible solubilizing aids are especially useful herein: alkoxylated ethers, and polyalkylene oxide polymers or copolymers. The alkoxylated ethers useful herein are of the formula:

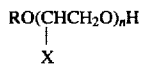

wherein R is straight or branched chain $C_1$ to $C_{18}$, preferably $C_1$ to $C_5$, and most preferably $C_1$ to $C_4$, and X is methyl or ethyl and n has an average value of from about 5 to about 20, preferably from about 8 to about 16, and more preferably from about 10 to about 16. Preferred compounds for use herein are the polyoxypropylene butyl ethers (i.e. where R is $C_4$). These compounds are also known as PPG butyl ethers. A preferred compound among these butyl ether derivatives is PPG-14 butyl ether (i.e. a butyl ether having about 14 propylene oxide units incorporated in its structure). PPG-14 butyl ether is available as Fluid AP from Union Carbide. Alternatively, another preferred compound is PPG-15 stearyl ether (i.e. a stearyl ether having about 15 propylene oxide units incorporated in its structure). PPG-15 stearyl ether is available as Arlamol S3 and S7 from ICI Americas.

The polyalkylene oxide polymers or copolymers useful herein include polypropylene oxides, polybutylene oxides, mixed polyethylene and polyproylene oxides, mixed polyethylene and polybutylene oxides, and the like, provided that the water-immiscibility requirement is met. Nonlimiting examples of these polymers include PPG-9, PPG-15, PPG-17, PPG-20, PPG-26, PPG-30, PPG-34, a copolymer of ethylene oxide and propylene oxide wherein the copolymer has an average of 3 ethylene oxide units and an average of 20 propylene oxide units, and a copolymer of propylene oxide and butylene oxide wherein the copolymer has an average of 10 propylene oxide units and an average of 5 butylene oxide units.

In other embodiments, the water-immiscible solubilizing aids include those of the above chemical formula wherein R is a straight or branched chain C1–C8 moiety having one or more free hydroxyl groups, wherein this moiety can be derived from the corresponding alcohol. Nonlimiting examples of these C1–C8 moieties include those derived from glycerin, propylene glycol, butylene glycol, hexylene glycol, 1,2,6-hexanetriol, and the like.

Vehicle

The compositions of the present invention are used along with pharmaceutically-acceptable carrier (or vehicle) components. The term "pharmaceutically-acceptable carrier components", as used herein, means compatible solid or liquid filler diluents which are suitable for administration to a human or lower animal. The term "compatible", as used herein, means that the components are capable of being commingled with the drug compounds, and other components of the compositions of the present invention, in a manner such that there is no interaction which would substantially reduce the pharmaceutical efficacy of the compositions of the present invention under ordinary use situations.

Pharmaceutically-acceptable carrier components must, of course, be of sufficiently high purity and sufficiently low toxicity to render them suitable for administration to the human or lower animal being treated.

Some examples of substances which can serve as pharmaceutically-acceptable carrier components are glycerol; ethanol; water; antioxidants; surfactants; chelating agents; preservatives; thickeners; anti-bacterial agents; as well as other non-toxic compatible substances used in pharmaceutical formulations.

These compositions can also contain one or more additional humectants/moisturizers, many of which may also be useful as actives. A variety of humectants/moisturizers can be employed and can be present at a level of from about 0.5% to about 30%, more preferably from about 2% to about 8%, and most preferably from about 3% to about 5%. These materials include polyhydroxy alcohols such as sorbitol, glycerin, hexanetriol, hexylene glycol and the like; sugars and starches; sugar and starch derivatives (e.g. alkoxylated glucose); D-panthenol and its derivatives; hyaluronic acid; lactamide monoethanolamine; acetamide monoethanolamine; and mixtures thereof. Other useful humectants include propylene oxide ethers of glyerin, preferably those having less than about four moles of propylene oxide per mole of glycerin. Useful examples of these propylene oxide ethers of glycerin are described in detail in U.S. Pat. No. 4,976,953, to Orr et al., issued Dec. 11, 1990, which is incorporated by reference herein.

Preferred humectants/moisturizers for use in the compositions of the present invention are the $C_3$–$C_6$ diols and triols. Especially preferred is the triol, glycerin.

The compositions of the present invention can also optionally comprise at least one emollient. Examples of suitable emollients include, but are not limited to, volatile and non-volatile silicone oils, highly branched hydrocarbons, and mixtures thereof. Emollients useful in the instant invention are further described in U.S. Pat. No. 4,919,934, to Deckner et al., issued Apr. 24 1990, which is incorporated herein by reference in its entirety.

The emollients can typically comprise in total from about 1% to about 50%, preferably from about 1% to about 25%, and more preferably from about 1% to about 10% by weight of the compositions of the present invention.

The compositions of this invention may also contain pharmaceutically acceptable optional components that modify the physical and/or therapeutic effects of the compositions. Such optional components may include, for example, additional solvents, gelling agents, fragrances, preservatives, anti-bacterial agents, thickeners (e.g., fatty alcohols such as cetyl alcohol and stearyl alcohol), and stabilizers. However, such optional materials must not unduly interfere with the transdermal delivery of the drug active. Optional components useful in the compositions of this invention are described in the following patent documents, incorporated by reference herein: European Patent Publication 43,738, Wickett et al., published Jan. 13, 1982; and U.S. Pat. No. 4,552,872, Cooper et al., issued Nov. 12, 1985.

Most preferred compositions herein are creams and lotions.

Another optional material is a solvent or co-solvent material.

Most preferred compositions herein have a pH of below about 5, preferably below about 4, and most preferably below about 3. Without being limited by theory, the pH of a formulation can be an important factor in the delivery and availability of an active ingredient. For example, for the active ingredient salicylic acid, at pH values above its $pK_a$ in a particular matrix, the salicylic acid would exist primarily in its ionized form and would not as readily penetrate into the skin. Thus, an acidic formulation range is preferred for salicylic acid compositions in order to supress ionization and enhance its penetration into the stratum corneum.

A wide variety of acids, bases, buffers, and sequestrants can be utilized to adjust and/or maintain the pH and ionic strength of the compositions useful in the instant invention. Materials useful for adjusting and/or maintaining the pH and/or the ionic strength include sodium carbonate, sodium hydroxide, hydrochloric acid, phosphoric acid, sulfuric acid, acetic acid, sodium acetate, sodium hydrogen phosphate, sodium dihydrogen phosphate, citric acid, sodium citrate, sodium bicarbonate, triethanolamine, EDTA, disodium EDTA, tetrasodium EDTA, and the like.

While particular embodiments of the present invention have been described, it will be obvious to those skilled in the art that various changes and modifications to the compositions disclosed herein can be made without departing from the spirit and the scope of the invention. It is intended to cover, in the appended claims, all such modifications that are within the scope of this invention.

Test Method

Transdermal penetration of drugs is conveniently determined and compared from various vehicles using the apparatus and procedure described below.

Full thickness excised human thigh skin is obtained from cadavers after all hair had been clipped and the skin washed. The skin samples are then bathed in 10% glycerin and stored frozen. The glycerin prevents the formation of ice crystals which could possibly damage the keratinized cells and/or the intercellular lipid matrix. After a rapid thawing, the skin is conditioned for 24 hours in Hank's Balanced Salt Solution with 1% antibacterial-antimycotic solution. Then the skin is washed with distilled water. A single skin donor is used for each experiment, and individual sections for use are selected based on integrity of the stratum corneum (visual determination). Selected areas are cut to 1 cm² using a scalpel.

Tests are conducted using glass diffusion cells placed in temperature-regulated stirring modules. Skin sections are mounted in the cells, and the receptor phase is added. The receptor phase is 50% Hank's Balance Salt Solution (including 1% antibiotic-antimycotic solution) and 50% ethanol. Each diffusion cell has an exposed area of 0.79cm² and a receptor capacity of 5 ml. Sufficient formulation is applied (750 ul) to the surface of the skin to ensure infinite dose conditions, and the diffusion cell is covered with plastic wrap or parafilm to prevent product evaporation. At each sampling time the receptor phase is removed for analysis of drug content. The receptor phase is removed for analysis of drug content. The receptor phase is replenished at each sampling time in order to maintain sink conditions. Preferably 3 to 6 replicates are run with sampling intervals occurring at 1, 2, 4 & 6 hours.

Penetration rate (Flux) is determined as the quantity of drug penetrating a measured area of skin per hour during the 5 hour interval between 1 hour and 6 hours. Generally steady state is reached before 1 hour. Penetration rate is usually expressed as ug drug per cm² skin per hour.

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLES

Example I

An anti-acne composition is made by combining the following components using conventional mixing technology.

| Ingredient | (% W/W) |
| --- | --- |
| Water, Purified | qs to 100 |
| PPG-14 Butyl Ether | 8.0 |
| Polyquaternium-32 and Mineral Oil[1] | 2.5 |
| Polyoxyethylene 10 Cetyl Ether | 0.75 |
| Salicylic Acid | 2.0 |
| Stearyl Alcohol | 0.75 |
| Cetyl Alcohol | 0.75 |
| 85% 5 cs Dimethyl Fluid/ 15% Dimethiconol[2] | 0.5 |
| Aluminum Starch Octenyl Succinate | 0.5 |

[1]SalCare SC92 available from Allied Colloids (Suffolk, VA).
[2]Dow Q2-1403 Fluid available from Dow Corning.

The PPG-14 Butyl ether, salicyclic acid, Polyoxyethylene 10 Cetyl Ether, and waxes are combined and heated until the waxes melt (e.g., up to about 75 C) and is mixed using a Lightnin' Mixer with a 3 blade paddle prop at a low speed (100 rpm). Water is added to this mixture. While mixing at a moderate speed (300 rpm), the polyquaternium-32 and mineral oil is added to the mixture. The resulting cream is mixed at moderate speed until uniform.

The composition displays skin penetration of the salicylic acid active with low dermal irritation as well as improved skin feel and residue characteristics together with excellent moisturizing, emolliency, rub-in and absorption characteristics.

Alternatively, the above composition is prepared by substituting the polyquaternium-32 and mineral oil with crosslinked methyl quaternized dimethylaminoethyl methacrylate and mineral oil [i.e. polyquaternium 37 (and) mineral oil (and) PPG-1 trideceth-6], available as SalCare SC95 from Allied Colloids (Suffolk, Va.).

Example II

An anti-acne and/or analgesic composition is made by combining the following ingredients utilizing conventional mixing techniques as described above in Example I.

| Ingredient | (% W/W) |
| --- | --- |
| Water, Purified | qs to 100 |
| Ibuprofen | 2.0 |
| Polyquaternium-32 and | 4.0 |

17
-continued

| Ingredient | (% W/W) |
|---|---|
| Mineral Oil[1] | |
| Polyoxyethylene 10 Cetyl Ether | 0.75 |
| Stearyl Alcohol | 0.75 |
| Cetyl Alcohol | 0.75 |
| 85% 5 cs Dimethyl Fluid/ | 0.5 |
| 15% Dimethiconol[2] | |
| Aluminum Starch Octenyl Succinate | 0.5 |

[1]SalCare SC92 available from Allied Colloids (Suffolk, VA).
[2]Dow Q2-1403 Fluid available from Dow Corning.

The compositions display skin penetration of the Ibuprofen active as well as improved skin feel and residue characteristics together with excellent moisturizing, emolliency, rub-in and absorption characteristics.

Alternatively, the above composition is prepared by substituting the polyquaternium-32 and mineral oil with crosslinked methyl quaternized dimethylaminoethyl methacrylate (and) mineral oil [i.e. polyquaternium 37 (and)mineral oil (and) PPG-1 trideceth-6], available as SalCare SC95 from Allied Colloids (Suffolk, Va.).

Example III

An anti-acne cream is made by combining the following components using conventional mixing technology.

| Ingredient | (% W/W) |
|---|---|
| Water, Purified | qs to 100 |
| PPG-14 Butyl Ether | 8.0 |
| Crosslinked Methyl Quaternized Dimethylaminoethyl Methacrylate and Mineral Oil[1] | 1.5 |
| Steareth-21 | 0.50 |
| Salicylic Acid | 2.0 |
| Stearyl Alcohol | 1.5 |
| Cetyl Alcohol | 1.5 |
| 85% 5 cs Dimethyl Fluid/ | 0.5 |
| 15% Dimethiconol[2] | |
| Dimethicone 200 | 0.6 |
| Glycerin | 3.0 |
| Citric Acid | 0.7 |
| Sodium Citrate | 0.3 |

[1]SalCare SC95 available from Allied Colloids (Suffolk, VA).
[2]Dow Q2-1403 Fluid available from Dow Corning In a vessel the cetyl alcohol, stearyl alcohol, steareth-21, and dimethicone 200 are heated to 70° C. In another vessel the PPG-14 butyl ether and salicyclic acid are combined and heated to 70° C. to dissolve the salicylic acid. This salicylic acid solution is then added with stirring to the cetyl alcohol mixture. Next the crosslinked methyl quaternized dimethylaminoethyl methacrylate polymer is added with stirring to the cetyl alcohol mixture. In a separate vessel, the water, glycerin, citric acid, and sodium citrate are combined and heated with stirring to 70° C. The cetyl alcohol mixture is then added with mixing to the water mixture to form the emulsion. Finally, the dimethyl fluid/dimethicone mixture is added with mixing and the mixture is then cooled to room temperature with mixing.

The resulting cream composition displays skin penetration of the salicylic acid active with low dermal irritation as well as improved skin feel and residue characteristics together with excellent moisturizing, emolliency, rub-in and absorption characteristics.

Alternatively, the above composition is prepared by substituting the methyl quaternized dimethylaminoethyl methacrylate and mineral oil with polyquaterniun-32 and mineral oil [i.e. polyquaternium 37 (and) mineral oil (and) PPG-1 trideceth-6], available as SalCare SC92 from Allied Colloids (Suffolk, Va.).

Example IV

A keratolytic composition for dermatological disorders is made by combining the following ingredients utilizing conventional mixing techniques as described above in Example I.

| Ingredient | (% W/W) |
|---|---|
| Water | qs to 100 |
| Urea | 10.0 |
| Polyquaternium-32 and Mineral Oil[1] | 4.0 |
| Polyoxyethylene 10 Cetyl Ether | 0.75 |
| Stearyl Alcohol | 0.75 |
| Cetyl Alcohol | 0.75 |
| 85% 5 cs Dimethyl Fluid/ | 0.5 |
| 15% Dimethiconol[2] | |
| Aluminum Starch Octenyl Succinate | 0.5 |

[1]SalCare SC92 available from Allied Colloids (Suffolk, VA).
[2]Dow Q2-1403 Fluid available from Dow Corning.

The compositions display skin penetration of the Urea active as well as improved skin feel and residue characteristics together with excellent moisturizing, emolliency, rub-in and absorption characteristics.

Alternatively, the above composition is prepared by substituting the polyquaternium-32 and mineral oil with crosslinked methyl quaternized dimethylaminoethyl methacrylate and mineral oil [i.e. polyquaternium 37 (and) mineral oil (and) PPG-1 trideceth-6], available as SalCare SC95 from Allied Colloids (Suffolk, Va.).

Example V

A composition for sunless tanning is made by combining the following ingredients utilizing conventional mixing techniques as described above in Example I.

| Ingredient | (% W/W) |
|---|---|
| Water | qs to 100 |
| Polyquaternium-32 and Mineral Oil[1] | 3.0 |
| Dihydroxyacetyone | 3.0 |
| Glycerin | 2.0 |
| Polyoxyethylene 10 Cetyl Ether | 0.75 |
| Stearyl Alcohol | 0.75 |
| Cetyl Alcohol | 0.75 |
| 85% 5 cs Dimethyl Fluid/ | 0.5 |
| 15% Dimethiconol[2] | |
| Aluminum Starch Octenyl Succinate | 0.5 |

[1]SalCare SC92 available from Allied Colloids (Suffolk, VA).
[2]Dow Q2-1403 Fluid available from Dow Corning.

The compositions display improved skin penetration of the dihydroxyacetone as well as improved skin feel and residue characteristics together with excellent moisturizing, emolliency, rub-in and absorption characteristics.

Alternatively, the above composition is prepared by substituting the polyquaternium-32 and mineral oil with crosslinked methyl quaternized dimethylaminoethyl methacrylate and mineral oil [i.e. polyquaternium 37 (and) mineral oil (and) PPG-1 trideceth-6], available as SalCare SC95 from Allied Colloids (Suffolk, Va.).

Example VI

A composition for sunless tanning which also contains sunscreens is made by combining the following ingredients utilizing conventional mixing techniques as described above in Example I.

| Ingredient | (% W/W) |
| --- | --- |
| Water | qs to 100 |
| Polyquaternium-32 and Mineral Oil[1] | 3.0 |
| Dihydroxyacetyone | 3.0 |
| Octyl Methoxycinnamate | 7.5 |
| Octyl Salicyliate | 1.0 |
| Glycerin | 2.0 |
| Polyoxyethylene 10 Cetyl Ether | 0.75 |
| Stearyl Alcohol | 0.75 |
| Cetyl Alcohol | 0.75 |
| 85% 5 cs Dimethyl Fluid/ 15% Dimethiconol[2] | 0.5 |
| Aluminum Starch Octenyl Succinate | 0.5 |

[1]SalCare SC92 available from Allied Colloids (Suffolk, VA).
[2]Dow Q2-1403 Fluid available from Dow Corning.

The compositions display improved skin penetration of the dihydroxyacetone as well as improved skin feel and residue characteristics together with excellent moisturizing, emolliency, rub-in and absorption characteristics. This composition also provides protection against the harmful effects of UV radiation.

Alternatively, the above composition is prepared by substituting the polyquaternium-32 and mineral oil with crosslinked methyl quaternized dimethylaminoethyl methacrylate and mineral oil [i.e. polyquaternium 37 (and) mineral oil (and) PPG-1 trideceth-6], available as SalCare SC95 from Allied Colloids (Suffolk, Va.).

Example VII

An anti-acne lotion is made by combining the following components using conventional mixing technology.

| Ingredient | (% W/W) |
| --- | --- |
| Water Phase | |
| Water, Purified | qs to 100 |
| Glycerin | 3.0 |
| Triethanolamine | 0.15 |
| Tetrasodium EDTA | 0.02 |
| Oil Phase | |
| PPG-14 Butyl Ether | 8.0 |
| Salicylic Acid | 2.0 |
| Crosslinked Methyl Quaternized Dimethylaminoethyl Methacrylate and mineral oil[1] | 1.5 |
| Cetyl Alcohol | 0.75 |
| Stearyl Alcohol | 0.75 |
| Dimethicone[2] | 0.60 |
| Steareth-21 | 0.45 |
| Steareth-2 | 0.05 |
| Fragrance Phase | |
| Fragrance | 0.08 |
| Cyclomethicone (and) dimethiconol[3] | 0.50 |

[1]SalCare SC95 [i.e. polyquaternium 37 (and) mineral oil (and) PPG-1 trideceth-6] available from Allied Colloids (Suffolk, VA).
[2]Dow Corning 200/350 centistokes available from Dow Corning.

In an appropriate vessel the water phase ingredients are combined and heated with stirring to about 75° C. In a separate vessel the oil phase ingredients are combined and heated with stirring to about 75° C. The oil phase is then added with stirring to the water phase to form an emulsion. Stirring is continued as the mixture is cooled to about 40° C. The fragrance phase is added and the mixture is cooled to room temperature with stirring.

The composition displays skin penetration of the salicylic acid active with low dermal irritation as well as improved skin feel and residue characteristics together with excellent moisturizing, emolliency, rub-in and absorption characteristics.

In an alternate method of preparation, the crosslinked methyl quaternized dimethylaminoethyl methacrylate and mineral oil is not added to the oil phase, but is instead added after the emulsion has been both formed and subsequently cooled to about 40° C.

Alternatively, the above composition is prepared by substituting the crosslinked methyl quaternized dimethylaminoethyl methacrylate and mineral oil with polyquaternium-32 and mineral oil, available as SalCare SC92 from Allied Colloids (Suffolk, Va).

Example VIII

An anti-acne cream is made by combining the following components using conventional mixing technology.

| Ingredient | (% W/W) |
| --- | --- |
| Water Phase | |
| Water, Purified | qs to 100 |
| Glycerin | 3.0 |
| Triethanolamine | 0.15 |
| Tetrasodium EDTA | 0.02 |
| Oil Phase | |
| PPG-14 Butyl Ether | 8.0 |
| Salicylic Acid | 2.0 |
| Crosslinked Methyl Quaternized Dimethylaminoethyl Methacrylate and mineral oil[1] | 1.5 |
| Cetyl Alcohol | 1.50 |
| Stearyl Alcohol | 1.50 |
| Dimethicone[2] | 0.60 |
| Steareth-21 | 0.45 |
| Steareth-2 | 0.05 |
| Fragrance Phase | |
| Fragrance | 0.08 |
| Cyclomethicone (and) dimethiconol[3] | 0.50 |

[1]SalCare SC95 [i.e. polyquaternium 37 (and) mineral oil (and) PPG-1 trideceth-6] available from Allied Colloids (Suffolk, VA).
[2]Dow Corning 200/350 centistokes available from Dow Corning.
[3]Dow Q2-1401 Fluid available from Dow Corning.

In an appropriate vessel the water phase ingredients are combined and heated with stirring to about 75° C. In a separate vessel the oil phase ingredients are combined and heated with stirring to about 75° C. The oil phase is then added with stirring to the water phase to form an emulsion. Stirring is continued as the mixture is cooled to about 40° C. The fragrance phase is added and the mixture is cooled to room temperature with stirring.

The composition displays skin penetration of the salicylic acid active with low dermal irritation as well as improved skin feel and residue characteristics together with excellent moisturizing, emolliency, rub-in and absorption characteristics.

In an alternate method of preparation, the crosslinked methyl quaternized dimethylaminoethyl methacrylate and mineral oil is not added to the oil phase, but is instead added after the emulsion has been both formed and subsequently cooled to about 40° C.

Alternatively, the above composition is prepared by substituting the crosslinked methyl quaternized dimethylaminoethyl methacrylate and mineral oil with polyquaternium-32 and mineral oil, available as SalCare SC92 from Allied Colloids (Suffolk, Va.).

Example IX

A salicylic acid containing cream is made by combining the following components using conventional mixing technology.

| Ingredient | (% W/W) |
|---|---|
| Water Phase | |
| Water, Purified | qs to 100 |
| Glycerin | 3.0 |
| Triethanolamine | 0.15 |
| Tetrasodium EDTA | 0.02 |
| Oil Phase | |
| PPG-14 Butyl Ether | 16.0 |
| Salicylic Acid | 4.0 |
| Crosslinked Methyl Quaternized Dimethylaminoethyl Methacrylate and mineral oil[1] | 3.0 |
| Cetyl Alcohol | 0.75 |
| Stearyl Alcohol | 0.75 |
| Dimethicone[2] | 0.60 |
| Steareth-21 | 0.45 |
| Steareth-2 | 0.05 |
| Fragrance Phase | |
| Fragrance | 0.08 |
| Cyclomethicone (and) dimethiconol[3] | 0.50 |

[1]SalCare SC95 [i.e. polyquaternium 37 (and) mineral oil PPG-1 trideceth-6] available from Allied Colloids (Suffolk, VA).
[2]Dow Corning 200/350 centisiokes available from Dow Corning.
[3]Dow Q2-1401 Fluid available from Dow Corning.

In an appropriate vessel the water phase ingredients are combined and heated with stirring to about 75° C. In a separate vessel the oil phase ingredients are combined and heated with stirring to about 75° C. The oil phase is then added with stirring to the water phase to form an emulsion. Stirring is continued as the mixture is cooled to about 40° C. The fragrance phase is added and the mixture is cooled to room temperature with stirring.

The composition displays skin penetration of the salicylic acid active with low dermal irritation as well as improved skin feel and residue characteristics together with excellent moisturizing, emolliency, rub-in and absorption characteristics.

In an alternate method of preparation, the crosslinked methyl quaternized dimethylaminoethyl methacrylate and mineral oil is not added to the oil phase, but is instead added after the emulsion has been both formed and subsequently cooled to about 40° C.

Alternatively, the above composition is prepared by substituting the crosslinked methyl quaternized dimethylaminoethyl methacrylate and mineral oil with polyquaternium-32 and mineral oil, available as SalCare SC92 from Allied Colloids (Suffolk, Va.).

What is claimed is:

1. A topical pharmaceutical composition having enhanced penetration through the skin, comprising:

(a) a safe and effective amount of a pharmaceutical active;

(b) from about 0.1% to about 10.0% of a high molecular weight crosslinked cationic polymer of the formula: $(A)_l(B)_m(C)_n$ wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is acrylamide, 1 is an integer of 0 or greater, m is an integer of 1 or greater, and n is an integer of 0 or greater, wherein said polymer contains a crosslinking agent;

(c) from about 0.05% to about 5% of a high HLB non-ionic surfactant;

(d) from about 0.1% to about 25% of an alkoxylated ether of the formula:

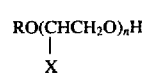

wherein R is straight or branched chain $C_1$ to $C_{18}$, and X is methyl or ethyl, and wherein n has an average value of from about 5 to about 20; and (e) a balance of a pharmaceutically acceptable vehicle comprising a major amount of water.

2. The composition of claim 1 wherein said high HLB nonionic surfactant is selected from ethoxylated alcohols having from about 8 to about 22 carbons and from about 6 to about 30 ethylene oxide groups.

3. The composition of claim 2 wherein said high HLB nonionic surfactant is selected from the group consisting of ceteth-10, steareth-21, and mixtures thereof.

4. The composition of claim 3 wherein said alkoxylated ether is selected from the group consising of PPG-14 butyl ether, PPG-15 stearyl ether, and mixtures thereof.

5. The composition of claim 4 wherein said pharmaceutical active is selected from the group consisting of anti-acne drugs, anti-wrinkle actives, anti-skin atrophy actives, non-steroidal anti-inflammatory drugs, steroidal anti-inflammatory drugs, sunless tanning agents, sunscreen agents, wound healing agents, skin bleaching or lightening agents, antihistaminic drugs, antitussive drugs, antipruritic drugs, anticholinergic drugs, anti-emetic and antinauseant drugs, anorexic drugs, central stimulant drugs, antiarrhythmic drugs, B-adrenergic blocker drugs, cardiotonic drugs, antihypertensive drugs, diuretic drugs, vasodilator drugs, vasoconstrictor drugs, anti-ulcer drugs, anesthetic drugs, antidepressant drugs, tranquilizer and sedative drugs, antipsychotic drugs, antimicrobial drugs, antineoplastic drugs, antimalarial drugs, muscle relaxant drugs, antispasmodic drugs, antidiarrheal drugs and bone-active drugs and mixtures thereof.

6. The composition of claim 5 wherein said pharmaceutical active is an anti-acne drug selected from the group consisting of salicylic acid, sulfur, resorcinol, N-acetylcysteine, octopirox, retinoic acid and its derivatives, benzoyl peroxide, erythromycin, zinc, tetracyclin, azelaic acid and its derivatives, phenoxy ethanol and phenoxy proponol, ethylacetate, clindamycin and meclocycline, flavinoids, lactic acid, glycolic acid, pyruvic acid, urea, scymnol sulfate and its derivatives, deoxycholate and cholate and mixtures thereof, or an anti-wrinkle active or anti-skin atrophy active selected from the group consisting of glycolic acid, lactic acid, salicylic acid, and mixtures thereof.

7. The composition of claim 5 wherein said pharmaceutical active is selected from the group consisitng of salicylic acid, glycolic acid, lactic acid, and mixtures thereof.

8. The composition of claim 7 wherein the amount of (C) in the cationic polymer is from about 50% to about 90% molar.

9. The composition of claim 7 wherein l in the cationic polymer is zero and the ratio of (B):(C) is from about 45:55 to about 55:45.

10. The composition of claim 7 wherein both l and n are zero in the cationic polymer.

11. The composition of claim 10 which further comprises from about 3% to about 5% glycerin.

12. The composition of claim 11 which further comprises from about 1% to about 10% of an emollient selected from the group consisting of volatile silicone oils, non-volatile silicone oils, highly branched hydrocarbons, and mixtures thereof.

13. The composition of claim 5 wherein said antihistaminic drug is selected from the group consisting of chlorpheniramine maleate, chlorpheniramine tannate, triprolidine hydrochloride, triprolidine oxalate, diphenhydramine hydrochloride, diphenhydramine ascorbate, diphenhydramine citrate, doxylamine succinate, pyrilamine maleate, pyrilamine hydrochloride, pyrilamine tannate, phenindamine tartrate, promethazine hydrochloride, cyproheptadine hydrochloride, azatadine maleate, clemastine fumarate, carbinoxamine maleate, carbinoxamine hydrochloride, tripelennamine hydrochloride, tripelennamine citrate, dexchlorpheniramine maleate, brompheniramine maleate and chlorcyclizine hydrochloride and mixtures thereof.

14. The composition of claim 5 wherein said antitussive drug is selected from the group consisting of dextromethorphan hydrobromide, carbetapentane citrate, codeine phosphate and codeine N-oxide hydrochloride and mixtures thereof.

15. The composition of claim 5 wherein said anticholinergic drug is selected from the group consisting of scopolamine hydrobromide, scopolamine hydrochloride, atropine sulfate, atropine mucate, homatropine hydrobromide and homatropine hydrochloride and mixtures thereof.

16. The composition of claim 5 wherein said anti-emetic or antinauseant drug is selected from the group consisting of cyclizine hydrochloride, meclizine hydrochloride, chlorpromazine hydrochloride and chlorpromazine maleate and mixtures thereof.

17. The composition of claim 5 wherein said anorexic drug is selected from the group consisting of benzphetamine hydrochloride, phentermine hydrochloride, chlorphentermine hydrochloride and fenfluramine hydrochloride and mixtures thereof.

18. The composition of claim 5 wherein said antimicrobial drug is selected from the group consisting of β-lactam drugs, quinolone drugs, ciprofloxacin, norfloxacin, tetracycline, erythromycin, hexamidine isethionate, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole and amanfadine, pharmaceutically-acceptable salts thereof and mixtures thereof.

19. The composition of claim 5 wherein said antiarrhythmic drug is selected from the group consisting of propranolol hydrochloride, procainamide hydrochloride, quinidine sulfate and quinidine gluconate and mixtures thereof.

20. The composition of claim 5 wherein said antihypertensive drug is selected from the group consisting of enalapril maleate, clonidine hydrochloride, hydralazine hydrochloride and hydralazine sulfate and mixtures thereof.

21. The composition of claim 5 wherein said anesthetic or antipruritic drug is selected from the group consisting of lidocaine hydrochloride, bupivacaine hydrochloride, chlorprocaine hydrochloride, dibucaine hydrochloride, etidocaine hydrochloride, mepivacaine hydrochloride, tetracaine hydrochloride, dyclonine hydrochloride and hexylcaine hydrochloride and mixtures thereof.

22. The composition of claim 5 wherein said bone-active drug is selected from the group consisting of 6-amino-1-hydroxyhexane-1,1-diphosphonic acid, 3-amino-1-hydroxypropanel,1-diphosphonic acid, octahydro-1-pyridine-6,6-diphosphonic acid, 2-(2'-piperidinyl)ethane-1,1-diphosphonic acid; 2-(3'-piperidinyl)-ethane-1,1-diphosphonic acid; 2-(2'-piperidinyl)-1-hydroxy-ethane-1, 1diphosphonic acid; 2-(3'-piperidinyl)-1-hydroxy-ethane-1, 1-diphosphonic acid; N-(2'-(3'-methyl)-piperidinylidene)-amino-methane diphosphonic acid; N-(2'-(1',3'-diazinylidene))-aminomethane diphosphonic acid; and N-(2-(3-methyl-piperidinylidene))-aminomethanephosphonomethylphosphinic acid, or esters thereof and mixtures thereof.

23. The composition of claim 5 wherein said non-steroidal anti-inflammatory drug is selected from the group consisting of propionic acid derivatives, acetic acid derivatives, fenamic acid derivatives, biphenylcarboxylic acid derivatives, and oxicams and mixtures thereof.

24. The composition of claim 5 wherein said non-steroidal anti-inflammatory drug is a propionic acid derivatives selected from the group consisting of aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid and mixtures thereof.

25. The composition of claim 5 wherein said drug active is a sunless tanning agent selected from the group consisting of dihydroxyacetone, indole derivatives and mixtures thereof.

26. The composition of claim 25 which further comprises a sunscreen active selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

27. A topical pharmaceutical composition having enhanced penetration through the skin comprising:

(a) a safe and effective amount of a pharmaceutical active;

(b) from about 0.1% to about 10.0% of a high molecular weight crosslinked cationic polymer of the formula: $(A)_l(B)_m(C)_n$, wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is acrylamide, l is an integer of 0 or greater, m is an integer of 1 or greater, and n is an integer of 0 or greater, wherein said polymer contains a crosslinking agent;

(c) from about 0.05% to about 5% of a high HLB non-ionic surfactant;

(d) from about 0.01% to about 5% of a low HLB non-ionic surfactant;

(e) from about 0.1% to about 25% of an alkoxylated ether of the formula:

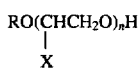

wherein R is straight or branched chain $C_1$ to $C_{18}$, and X is methyl or ethyl, and wherein n has an average value of from about 5 to about 20; and (f) a balance: of a pharmaceutically acceptable vehicle comprising a major amount of water.

28. The composition of claim 27 wherein the crosslinking agent is selected from the group consisting of methylene bisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, allyl acrylate, and mixtures thereof.

29. The composition of claim 28 wherein said crosslinking agent is methylbisacrylamide.

30. The composition of claim 29 wherein said high HLB nonionic surfactant is selected from ethoxylated alcohols having from about 8 to about 22 carbons and from about 6 to about 30 ethylene oxide groups.

31. The composition of claim 30 wherein said high HLB nonionic surfactant is selected from the group consisting of ceteth-10, steareth-21, and mixtures thereof.

32. The composition of claim 31 wherein said alkoxylated ether is selected from the group consising of PPG-14 butyl ether, PPG-15 stearyl ether, and mixtures thereof.

33. The composition of claim 32 wherein said low HLB nonionic surfactant is selected from ethoxylated alcohols having from about 8 to about 22 carbons and from about 1 to about 5 ethylene oxide groups.

34. The composition of claim 33 wherein said low HLB nonionic surfactant is selected from the group consisting of steareth-2, ceteth-2, laureth-2, oleth-2, and mixtures thereof.

35. The composition of claim 34 wherein said low HLB nonionic surfactant is steareth-2.

36. The composition of claim 35 wherein said pharmaceutical active is selected from the group consisting of anti-acne drugs, anti-wrinkle actives, anti-skin atrophy actives, non-steroidal anti-inflammatory drugs, steroidal anti-inflammatory drugs, sunless tanning agents, sunscreen agents, wound healing agents, skin bleaching or lightening agents, antihistaminic drugs, antitussive drugs, antipruritic drugs, anticholinergic drugs, anti-emetic and antinauseant drugs, anorexic drugs, central stimulant drugs, antiarrhythmic drugs, B-adrenergic blocker drugs, cardiotonic drugs, antihypertensive drugs, diuretic drugs, vasodilator drugs, vasoconstrictor drugs, anti-ulcer drugs, anesthetic drugs, antidepressant drugs, tranquilizer and sedative drugs, antipsychotic drugs, antimicrobial drugs, antineoplastic drugs, antimalarial drugs, muscle relaxant drugs, antispasmodic drugs, antidiarrheal drugs and bone-active drugs and mixtures thereof.

37. The composition of claim 35 wherein said pharmaceutical active is an anti-acne drug selected from the group consisting of salicylic acid, sulfur, resorcinol, N-acetylcysteine, octopirox, retinoic acid and its derivatives, benzoyl peroxide, erythromycin, zinc, tetracyclin, azelaic acid and its derivatives, phenoxy ethanol and phenoxy proponol, ethylacetate, clindamycin and meclocycline, flavinoids, lactic acid, glycolic acid, pyruvic acid, urea, scymnol sulfate and its derivatives, deoxycholate and cholate and mixtures thereof, or an anti-wrinkle active or anti-skin atrophy active selected from the group consisting of glycolic acid, lactic acid, salicylic acid, and mixtures thereof.

38. The composition of claim 35 wherein said pharmaceutical active is selected from the group consisting of salicylic acid, lactic acid, glycolic acid, and mixtures thereof.

39. The composition of claim 38 wherein the amount of (C) in the cationic polymer is from about 50% to about 90% molar.

40. The composition of claim 39 wherein l in the cationic polymer is zero and the ratio of (B):(C) is from about 45:55 to about 55:45.

41. The composition of claim 40 wherein both l and n are zero in the cationic polymer.

42. The composition of claim 41 which further comprises from about 3% to about 5% glycerin.

43. The composition of claim 42 which further comprises from about 1% to about 10% of an emollient selected from the group consisting of volatile silicone oils, non-volatile silicone oils, highly branched hydrocarbons, and mixtures thereof.

44. The composition of claim 36 wherein said drug active is a sunless tanning agent selected from the group consisting of dihydroxyacetone, indole derivatives and mixtures thereof.

45. The composition of claim 43 which further comprises a sunscreen active selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

* * * * *

UNITED STATES PATENT AND TRADEMARK OFFICE
CERTIFICATE OF CORRECTION

PATENT NO.    : 5,614,178
DATED         : March 25, 1997
INVENTOR(S)   : Roberta C. Bloom, George E. Deckner It is certified that error appears in the above-identified patent and that said Letters Patent is hereby corrected as shown below:

At column 4, line 11 "25° C." should read --25° C,--.

At column 9, line 33 "Registor" should read --Register--.

At column 11, line 31 "Of" should read --of--.

At column 17, line 20 "(and)mineral" should read --(and) mineral--.

At column 19, line 64 insert --³Dow Q2-1401 Fluid available from Dow Corning.--.

At column 22, line 7 "1 is an integer" should read --l is an integer--.

At column 25, line 9 "balance: of" should read --balance of--.

At column 26, line 41 "claim 43" should read --claim 44--.

Signed and Sealed this

Twenty-ninth Day of July, 1997

*Attest:*

BRUCE LEHMAN

*Attesting Officer*             *Commissioner of Patents and Trademarks*